United States Patent
West et al.

(10) Patent No.: US 10,820,948 B2
(45) Date of Patent: *Nov. 3, 2020

(54) SYSTEM AND METHOD FOR HOLOGRAPHIC IMAGE-GUIDED PERCUTANEOUS ENDOVASCULAR PERCUTANEOUS PROCEDURES

(71) Applicant: THE CLEVELAND CLINIC FOUNDATION, Cleveland, OH (US)

(72) Inventors: Karl West, Geneva, OH (US); Jeffrey H. Yanof, Solon, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/593,374

(22) Filed: Oct. 4, 2019

(65) Prior Publication Data

US 2020/0038117 A1 Feb. 6, 2020

Related U.S. Application Data

(63) Continuation of application No. 15/958,770, filed on Apr. 20, 2018, now Pat. No. 10,478,255.

(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 5/6852* (2013.01); *A61B 5/745* (2013.01);
(Continued)

(58) Field of Classification Search
CPC ....... A61B 34/20; A61B 90/361; A61B 90/37; A61B 34/25; G06T 7/344
See application file for complete search history.

(56) References Cited

U.S. PATENT DOCUMENTS 6,149,592 A 11/2000 Yanof et al.
10,194,131 B2 * 1/2019 Casas ................ G06F 3/0304
(Continued)

FOREIGN PATENT DOCUMENTS

EP 1803394 B1 1/2012
WO 2015/192117 A1 12/2015

OTHER PUBLICATIONS

Almefty, Rami O., and Peter Nakaji. "Augmented reality-enhanced navigation for extracranial-intracranial bypass." World neurosurgery 84.1 (2015): 15.

(Continued)

*Primary Examiner* — Sarah Lhymn
(74) *Attorney, Agent, or Firm* — Tarolli, Sundheim, Covell & Tummino LLP (57) ABSTRACT

Holographic image-guidance can be used to track an interventional device during an endovascular percutaneous procedure. The holographic image guidance can be provided by a head-mounted device by transforming tracking data and vasculature image data to a common coordinate system and creating a holographic display relative to a patient's vasculature to track the interventional device during the endovascular percutaneous procedure. The holographic display can also include graphics to provide guidance for the physical interventional device as it travels through the patient's anatomy (e.g., the vasculature).

20 Claims, 4 Drawing Sheets

Related U.S. Application Data (60) Provisional application No. 62/487,519, filed on Apr. 20, 2017.

(51) Int. Cl.

| | | |
|---|---|---|
| *A61B 5/00* | (2006.01) | |
| *G06T 17/20* | (2006.01) | |
| *G06T 3/00* | (2006.01) | |
| *G06T 3/20* | (2006.01) | |
| *G06F 3/01* | (2006.01) | |
| *G06T 7/33* | (2017.01) | |
| *A61B 90/00* | (2016.01) | |
| *G06K 9/32* | (2006.01) | |
| *G06K 9/00* | (2006.01) | |
| *A61M 5/00* | (2006.01) | |
| *A61B 34/00* | (2016.01) | |
| *A61B 34/10* | (2016.01) | |
| *A61B 90/50* | (2016.01) | |
| *G02B 27/01* | (2006.01) | |
| *G06T 19/00* | (2011.01) | |

(52) U.S. Cl.
CPC .......... *A61B 5/7405* (2013.01); *A61B 34/25* (2016.02); *A61B 90/361* (2016.02); *A61B 90/37* (2016.02); *A61M 5/00* (2013.01); *G06F 3/012* (2013.01); *G06K 9/00671* (2013.01); *G06K 9/3216* (2013.01); *G06T 3/0006* (2013.01); *G06T 3/20* (2013.01); *G06T 7/344* (2017.01); *G06T 17/20* (2013.01); *A61B 5/064* (2013.01); *A61B 2034/102* (2016.02); *A61B 2034/107* (2016.02); *A61B 2034/2051* (2016.02); *A61B 2034/2057* (2016.02); *A61B 2034/2068* (2016.02); *A61B 2090/363* (2016.02); *A61B 2090/365* (2016.02); *A61B 2090/366* (2016.02); *A61B 2090/367* (2016.02); *A61B 2090/368* (2016.02); *A61B 2090/372* (2016.02); *A61B 2090/3762* (2016.02); *A61B 2090/3983* (2016.02); *A61B 2090/502* (2016.02); *A61M 2205/507* (2013.01); *G02B 2027/0174* (2013.01); *G06K 2009/3225* (2013.01); *G06K 2209/05* (2013.01); *G06T 19/006* (2013.01)

(56) References Cited

U.S. PATENT DOCUMENTS

| | | |
|---|---|---|
| 2006/0142657 A1 | 6/2006 | Quaid et al. |
| 2008/0013809 A1 | 1/2008 | Zhu et al. |
| 2014/0189508 A1 | 7/2014 | Granchi et al. |
| 2015/0157416 A1* | 6/2015 | Andersson ............ A61B 34/20 606/102 |
| 2016/0324580 A1 | 11/2016 | Esterberg |
| 2017/0119474 A1* | 5/2017 | Kronman ............ A61B 1/00006 |
| 2017/0354342 A1 | 12/2017 | Ben-Yishai et al. |
| 2017/0367771 A1 | 12/2017 | Tako et al. |
| 2018/0185100 A1 | 7/2018 | Weinstein et al. |
| 2018/0200018 A1 | 7/2018 | Silva et al. |
| 2019/0333626 A1* | 10/2019 | Mansi ................ A61B 5/7405 |

OTHER PUBLICATIONS

Assis, Gilda Aparecida de, et al. "An augmented reality system for upper-limb post-stroke motor rehabilitation: a feasibility study." Disability and Rehabilitation: Assistive Technology 11.6 (2016): 521-528.

Badiali, Giovanni, et al. "Augmented reality as an aid in maxillofacial surgery: validation of a wearable system allowing maxillary repositioning." Journal of cranio-Maxillofacial surgery 42.8 (2014): 1970-1976.

Buchs, N. C., and R. Hompes. "Stereotactic navigation and augmented reality for transanal total mesorectal excision?." Colorectal Disease 17.9 (2015): 825-827.

Cabrilo, Ivan, et al. "Augmented reality-assisted skull base surgery." Neurochirurgie 60.6 (2014): 304-306.

Chen, Xiaojun, et al. "Development of a surgical navigation system based on augmented reality using an optical see-through head-mounted display." Journal of biomedical informatics 55 (2015): 124-131.

Floridi, Chiara, et al. "C-arm cone-beam computed tomography needle path overlay for percutaneous biopsy of pulmonary nodules." La radiologia medica 119.11 (2014): 820-827.

Fontaine-Delaruelle, C., et al. "Predictive factors of complications during CT-guided transthoracic biopsy." Revue de pneumologie clinique 73.2 (2017): 61-67.

Gruber-Rough, Tatjana, et al. "Computed tomography-guided biopsies in children: accuracy, efficiency and dose usage." Italian journal of pediatrics 43.1 (2017): 4.

Haas, Brian M., et al. "CT-guided percutaneous lung biopsies in patients with suspicion for infection may yield clinically useful information." American Journal of Roentgenology 208.2 (2017): 459-463.

Hu, Minxia, et al. "CT screening for lung cancer: Frequency of enlarged adrenal glands identified in baseline and annual repeat rounds." European radiology 26.12 (2016): 4475-4481.

Lee, Ha-Yeon, and In Jae Lee. "Assessment of independent risk factors of developing pneumothorax during percutaneous core needle lung biopsy: focus on lesion depth." Iranian Journal of Radiology 13.4 (2016).

Locklin, Julia K., et al. "Respiratory biofeedback during CT-guided procedures." Journal of Vascular and Interventional Radiology 18.6 (2007): 749-755.

Mckay, Tyler, et al. "Cone-beam CT with fluoroscopic overlay versus conventional CT guidance for percutaneous abdominopelvic abscess drain placement." Journal of Vascular and Interventional Radiology 27.1 (2016): 52-57.

Patz Jr, Edward F., et al. "Lung cancer incidence and mortality in National Lung Screening Trial participants who underwent low-dose CT prevalence screening: a retrospective cohort analysis of a randomised, multicentre, diagnostic screening trial." The Lancet Oncology 17.5 (2016): 590-599.

PCT International Search Report and Written Opinion for corresponding International Application Serial No. PCT/US2018/028615, dated Jul. 9, 2018, pp. 1-15.

PCT International Search Report and Written Opinion for corresponding International Application Serial No. PCT/US2018/028623, dated Jul. 9, 2018, pp. 1-15.

Quaife, Samantha L., et al. "The Lung Screen Uptake Trial (LSUT): protocol for a randomised controlled demonstration lung cancer screening pilot testing a targeted invitation strategy for high risk and 'hard-to-reach' patients." BMC cancer 16.1 (2016): 281.

Rotolo, Nicola, et al. "Comparison of cone-beam CT-guided and CT fluoroscopy-guided transthoracic needle biopsy of lung nodules." European radiology 26.2 (2016): 381-389.

Teles, Pedro, et al. "A review of radiation protection requirements and dose estimation for staff and patients in CT fluoroscopy." Radiation protection dosimetry 174.4 (2017): 518-534.

Uzun, Çaglar, et al. "Diagnostic accuracy and safety of CT-guided fine needle aspiration biopsy of pulmonary lesions with non-coaxial technique: a single center experience with 442 biopsies." Diagnostic and Interventional Radiology 23.2 (2017): 137.

Wood, Bradford J., et al. "Technologies for guidance of radiofrequency ablation in the multimodality interventional suite of the future." Journal of vascular and interventional radiology 18.1 (2007): 9-24.

Zemirline, Ahmed, et al. "Augmented reality-based navigation system for wrist arthroscopy: feasibility." Journal of wrist surgery 2.04 (2013): 294-298.

\* cited by examiner

SYSTEM AND METHOD FOR HOLOGRAPHIC IMAGE-GUIDED PERCUTANEOUS ENDOVASCULAR PERCUTANEOUS PROCEDURES

RELATED APPLICATIONS

This application is a continuation of U.S. Ser. No. 15/958,770, entitled "SYSTEM AND METHOD FOR HOLOGRAPHIC IMAGE-GUIDED PERCUTANEOUS ENDOVASCULAR PERCUTANEOUS PROCEDURES", filed Apr. 20, 2018, which claims the benefit of U.S. Provisional Application No. 62/487,519, filed Apr. 20, 2017, entitled "3D HOLOGRAPHIC GUIDANCE AND DEVICE NAVIGATION AUGMENTED TO THE INTERVENTIONAL SITE FOR PERCUTANEOUS PROCEDURES". These applications are hereby incorporated by reference in their entirety for all purposes.

GOVERNMENT FUNDING

This invention was made with government support under HL119810 awarded by the National Institutes of Health. The government has certain rights in the invention.

TECHNICAL FIELD

The present disclosure relates generally to endovascular percutaneous procedures and, more specifically, to systems and methods that provide holographic image-guidance for the endovascular percutaneous procedures.

BACKGROUND

Image-guided surgery (IGS), also known as surgical navigation, visually correlates intraoperative anatomy with a preoperative image in real-time (or "live"). Often, IGS is considered to be analogous to global position system (GPS), a technology that permits individuals to show their relative position on a computer-generated map. In IGS, the preoperative image can serve as the map, and the intraoperative tracking system is similar to the satellites and devices that are used for GPS. Using IGS provides greater control of a surgical procedure, real-time feedback on the effect of the intervention, and reduced trauma/disruption when accessing the surgical target.

The theoretical usefulness of IGS is limited in practice due to the visual correlation of the intraoperative anatomy with the preoperative image. Increased use of the intraoperative imaging would lead to greater confidence with avoiding critical structures and locating the target, but this leads to an increased radiation dose burden to the patient and the interventionist due to the real time fluoroscopy or computed tomography (CT). Additionally, images of the target and an interventional instrument are presently displayed on a flat, 2D monitor at tableside. To control the interventional instrument, the interventionist must translate its position and trajectory relative to the target viewed on a 2D monitor into physical trajectory adjustments that are needed to correct the path of the instrument. Current image-guidance techniques can lead to procedure related complications (such as hemorrhage). Moreover, the use of CT guidance for percutaneous procedures can affect revenue for the institution by reducing the number of diagnostic scans being performed (decreasing throughput).

SUMMARY

The present disclosure relates generally to endovascular percutaneous procedures and, more specifically, to systems and methods that provide holographic image-guidance for the endovascular percutaneous procedures.

In one aspect, the present disclosure can include a method for providing holographic image-guidance for an endovascular percutaneous procedure. The method can be performed by a head-mounted device that includes a processor, which can receive tracking data for a physical interventional device in a tracking coordinate system; transform the tracking data for the physical interventional device in the tracking coordinate system into a headset coordinate system; access image data from a pre-operative image of a patient's anatomy comprising a physical operative site in an imaging coordinate system; transform the image data in the imaging coordinate system into the headset coordinate system; register a 3D holographic representation of the interventional device based on the tracking data for the physical interventional device in the headset coordinate system to 3D anatomical holographic projections of the patient's anatomy based on the imaging data in the headset coordinate system; display the 3D anatomical holographic projections providing a visualization of a holographic version of the patient's anatomy with reference graphics related to a physical operative site within the patient's anatomy; display the 3D holographic representation of the interventional device providing a visualization of a holographic version of the interventional device with guidance control graphics related to the physical interventional device; and navigate the 3D holographic representation of the interventional device in the 3D anatomical holographic projections based on the tracking data for the interventional device in the headset coordinate system. The reference graphics and the guidance control graphics provide guidance for tracking the physical interventional device through the patient's anatomy using the 3D anatomical holographic projections and the 3D holographic representation of the interventional device.

In another aspect, the present disclosure can include a head-mounted device to holographic image-guidance for an endovascular percutaneous procedure. The head-mounted device includes a non-transitory memory that is accessed by the processor to execute instructions to perform operations. The operations include receiving tracking data for a physical interventional device in a tracking coordinate system; transforming the tracking data for the physical interventional device in the tracking coordinate system into a headset coordinate system; accessing image data from a pre-operative image of a patient's anatomy comprising a physical operative site in an imaging coordinate system; transforming the image data in the imaging coordinate system into the headset coordinate system; registering a 3D holographic representation of the interventional device based on the tracking data for the physical interventional device in the headset coordinate system to 3D anatomical holographic projections of the patient's anatomy based on the imaging data in the headset coordinate system; displaying the 3D anatomical holographic projections providing a visualization of a holographic version of the patient's anatomy with reference graphics related to a physical operative site within the patient's anatomy; displaying the 3D holographic representation of the interventional device providing a visualization of a holographic version of the interventional device with guidance control graphics related to the physical interventional device; and navigating the 3D holographic representation of the interventional device in the 3D anatomical holographic projections based on the tracking data for the interventional device in the headset coordinate system. The reference graphics and the guidance control graphics provide guidance for tracking the physical interventional device through the patient's anatomy using the 3D anatomical holographic projections and the 3D holographic representation of the interventional device.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "percutaneous" refers to something that is made, done, or effected through the skin.

As used herein, the term "percutaneous medical procedure" refers to accessing a component (e.g., vein, artery, or the like) of the vasculature through the skin, rather than by using an open approach where internal organs or tissues are exposed with the vasculature (typically with a scalpel).

As used herein, the term "endovascular" when used with "percutaneous medical procedure" refers to a medical procedure performed on a blood vessel (or the lymphatic system) accessed percutaneously. Examples of endovascular percutaneous medical procedures can include an aneurism repair, a stent grafting/placement, a placement of an endovascular prosthesis, a placement of a wire, a catheterization, a filter placement, an angioplasty, or the like.

As used herein, the term "interventional device" refers to a medical instrument used during the vascular percutaneous medical procedure.

As used herein, the term "tracking system" refers to something used to observe one or more objects undergoing motion and supply a timely ordered sequence of tracking data (e.g., location data, orientation data, or the like) in a tracking coordinate system for further processing. As an example, the tracking system can be an electromagnetic tracking system that can observe an interventional device equipped with a sensor-coil as the interventional device moves through a patient's vasculature.

As used herein, the term "tracking data" refers to information recorded by the tracking system related to an observation of one or more objects undergoing motion.

As used herein, the term "tracking coordinate system" refers to a 3D Cartesian coordinate system that uses one or more numbers to determine the position of points or other geometric elements unique to the particular tracking system. For example, the tracking coordinate system can be rotated, scaled, or the like, from a standard 3D Cartesian coordinate system.

As used herein, the term "head-mounted device" or "headset" refers to a display device, configured to be worn on the head, that has one or more display optics (including lenses) in front of one or more eyes. In some instances, the head-mounted device can also include a non-transitory memory and a processing unit. An example of a head-mounted device is a Microsoft HoloLens.

As used herein, the term "headset coordinate system" refers to a 3D Cartesian coordinate system that uses one or more numbers to determine the position of points or other geometric elements unique to the particular head-mounted device system. For example, the headset coordinate system can be rotated, scaled, or the like, from a standard 3D Cartesian coordinate system.

As used herein, the term "imaging system" refers to something that creates a visual representation of the interior of a patient's body (including the vasculature). In some instances, the imaging system can be 3D. For example, the imaging system can be a computed tomography (CT) system, a magnetic resonance imaging (MRI) system, an ultrasound (US) system, or the like.

As used herein, the term "image data" refers to information recorded in 3D by the imaging system related to an observation of the interior of the patient's body (including the vasculature). For example, the image data can include tomographic images represented by data formatted according to the Digital Imaging and Communications in Medicine (DICOM) standard (referred to as DICOM data herein).

As used herein, the term "imaging coordinate system" refers to a 3D Cartesian coordinate system that uses one or more numbers to determine the position of points or other geometric elements unique to the particular imaging system. For example, the imaging coordinate system can be rotated, scaled, or the like, from a standard 3D Cartesian coordinate system.

As used herein, the term "hologram", "holographic projection", or "holographic representation" refers to a computer-generated image projected to a lens of a headset. Generally, a hologram can be generated synthetically (in an augmented reality (AR)) and is not related to physical reality.

As used herein, the term "physical" refers to something real. Something that is physical is not holographic (or not computer-generated).

As used herein, the term "two-dimensional" or "2D" refers to something represented in two physical dimensions.

As used herein, the term "three-dimensional" or "3D" refers to something represented in three physical dimensions. An element that is "4D" (e.g., 3D plus a time and/or motion dimension) would be encompassed by the definition of three-dimensional or 3D.

As used herein, the term "reference graphics" refers to a holographic image related to a physical operative site within the patient's anatomy to aid in guidance of an interventional device.

As used herein, the term "guidance control graphics" refers to a holographic image related to an interventional device to aid in guidance of the interventional device.

As used herein, the term "integrated" can refer to two things being linked or coordinated. For example, a coil-sensor can be integrated with an interventional device.

As used herein, the term "degrees-of-freedom" refers to a number of independently variable factors. For example, a tracking system can have six degrees-of-freedom—a 3D point and 3 dimensions of rotation.

As used herein, the term "real-time" refers to the actual time during which a process or event occurs. In other words, a real-time event is done live (within milliseconds so that results are available immediately as feedback). For example, a real-time event can be represented within 100 milliseconds of the event occurring As used herein, the terms "subject" and "patient" can be used interchangeably and refer to any vertebrate organism.

II. Overview

The present disclosure relates generally to endovascular percutaneous procedures and, more specifically, to systems and methods that provide holographic image-guidance for the endovascular percutaneous procedures. The holographic image-guidance allows for real time navigation of a physical interventional device through a patient's vasculature to an interventional target. Tracking data (position and orientation) for the physical interventional device can captured using a tracking system to navigate the physical interventional device through the patient's vasculature. A 3D holographic interventional device can be projected within a 3D holographic anatomical image that is generated based on pre-operative images and navigated based on the tracking data. The 3D holographic interventional device can be displayed within the 3D holographic anatomical image due to the tracking data and the image data each being transformed into a coordinate system of a headset that displays the 3D holographic images.

Such holographic image-guidance is achieved using augmented reality (AR) to display 3D holographic projections at the interventional site in registration with the physical patient instead of displaying source images on a 2D monitor. The systems and methods of the present disclosure help to overcome limitations of traditional image guided procedures, which use CT and fluoroscopy. The use of holographic image-guidance leads to a shorter procedure time with less radiation dose to both the interventionalist and the patient, as well as fewer procedural complications caused by hitting critical structures during the procedure. Moreover, the holographic image-guidance allows for hands-free guidance and navigation that facilitates sterility of the surgical field. The use of holographic image-guidance can also increase revenue by allowing percutaneous procedures to be performed outside of a high-tech 3D CT suite, using less expensive (lower tech, such as 2D) guidance imaging, such as ultrasound and mobile C-arm fluoroscopy in conjunction with the holographic image-guidance.

III. Systems

One aspect of the present disclosure can include a system 10 (FIG. 1) that provides holographic image-guidance for endovascular percutaneous procedures. Endovascular percutaneous procedures can refer to any medical procedure performed on any portion of a subject's vasculature or lymphatic system that is accessed percutaneously (e.g., through the patient's upper leg or groin area). Examples of endovascular percutaneous medical procedures can include an aneurism repair procedure, a stent grafting/placement procedure, a catheterization procedure, a filter placement procedure, a wire placement procedure, an endovascular prosthesis placement procedure, an angioplasty procedure, a guidewire placement procedure, a minimally-invasive catheter procedure, an ablation procedure, a cryoablation procedure, or the like.

Figure 1:
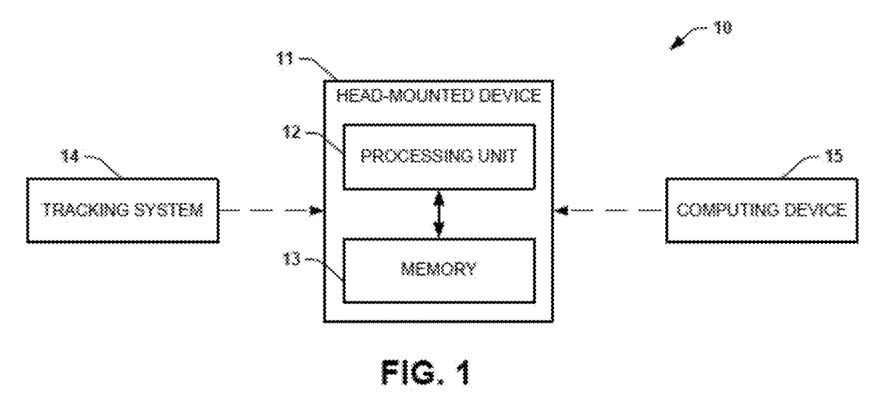
FIG. 1 is a block diagram illustration showing an example of a system that provides holographic image-guidance for endovascular percutaneous procedures in accordance with an aspect of the present disclosure.

The holographic image-guidance can use 3D augmented reality to replace or otherwise enhance traditional 2D image guidance. The system 10 can include a head-mounted device 11 that can be configured to facilitate the 3D augmented reality holographic display. The head-mounted device 11 can include a non-transitory memory 13 and a processing unit 12 (that may include one or more hardware processors) that can aid in the display of the holographic display. The head-mounted device can also include a camera to record one or more images, one or more image-generation components to generate/display a visualization of the hologram, and/or other visualization and/or recording elements.

The head-mounted device 11 can be in communication with a tracking system 14 to receive tracking data. The tracking system 14 can be an electromagnetic (EM) tracking system that can track the location and orientation of a physical interventional device. The physical interventional device can be integrated with one or more sensor-coils. For a non-rigid device (like many used in endovascular procedures), one or more sensor-coils can be located at a tip of the physical interventional device. However, for a non-rigid device the one or more sensor-coils can be located anywhere along the physical interventional device and need not be on the physical interventional device at all (e.g., may be located outside the patient's body). As the physical interventional device traverses a patient's vasculature, the tracking system 14 can detect the one or more sensor-coils and provide tracking data (e.g., with six degrees of freedom) in response to the detection. For example, the tracking data can include real-time 3D position data and real-time 3D orientation data. The tracking system can also detect coil-sensors that are not located on the physical interventional device (e.g., located on fiducial markers or other imaging targets). The tracking data can be recorded in a coordinate system of the tracking system 14 and sent (wirelessly and/or via a wired connection) to the head-mounted device 11.

The head-mounted device 11 can also be in communication with a computing device 15 to receive data related to a preoperative imaging study of at least a portion of the underlying anatomy. The preoperative imaging study can record 3D images (e.g., tomographic images) of the portion of the patient's anatomy. The 3D images can be represented by imaging data (which can be DICOM data), which can be formatted according to an imaging coordinate system of the certain imaging modality that was used to record the imaging data and sent to the head-mounted device 11.

Figure 2:
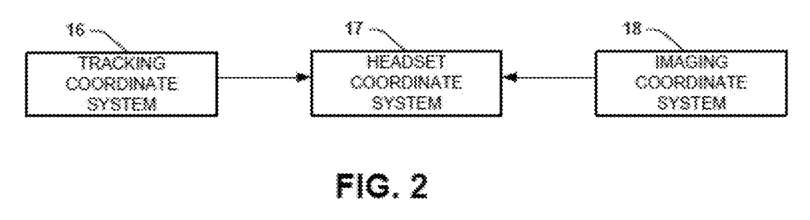
FIG. 2 is a block diagram illustration showing an example of the coordinate transformation accomplished by the head-mounted device of FIG. 1.

As shown in FIG. 2, the tracking coordinate system 16 and the imaging coordinate system 18 can each be transformed (e.g., translated and rotated) into the headset coordinate system 17. The transformation can be based on a rigid body affine transformation, for example. Accordingly, the tracking data in the tracking coordinate system 16 can be transformed (e.g., translated and rotated) into the headset coordinate system 18. Likewise, the imaging data in the imaging coordinate system 18 can be transformed (e.g., translated and rotated) into the headset coordinate system 18. Only when the tracking data and the imaging data is each transformed into the headset coordinate system can a visualization be generated showing a 3D holographic view illustrating the navigation of the physical interventional device within the patient's vasculature.

Figure 3:
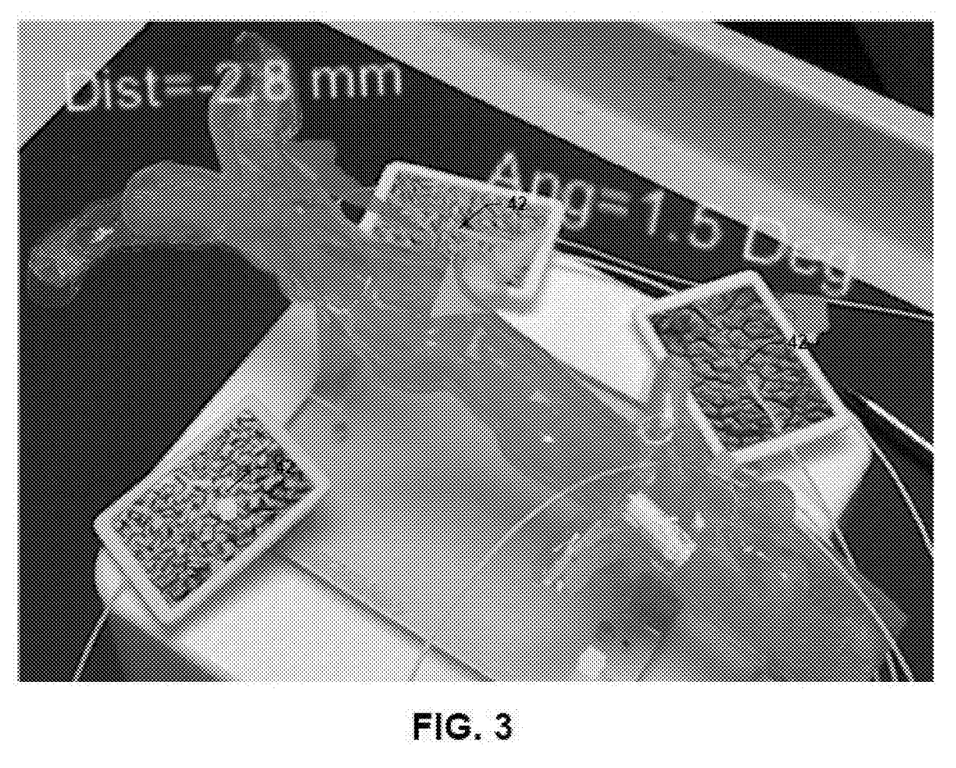
FIG. 3 is an illustration of an example of a hologram showing reference graphics and guidance control graphics used to control navigation of a physical interventional device through a physical vasculature using holographic image-guidance.

FIG. 3 is an image showing visualizations of the holographic image-guidance. FIG. 3 shows a hologram of a stent being implanted to a location in the vasculature (e.g., a model of the renal artery). The hologram includes guidance graphics and annotations showing tracking information. However, the guidance can be visual and/or auditory feedback related to location and orientation of the physical interventional device. The hologram includes guidance graphics and annotations showing tracking information. However, the guidance can be visual and/or auditory feedback related to location and orientation of the physical interventional device. FIG. 3 also shows three non-collinear fiducial markers 42 that are used for registration. The fiducial markers 42 can be combination markers so that the positions of the fiducial markers 42 can be detected in the tracking coordinate system and the headset coordinate system. Additionally, positions of the fiducial markers 42 can be located (e.g., sensor coils on the physical patient's skin). The positions of the fiducial markers can be matched to three or more locations in the image coordinate system.

The head-mounted device 11 can further transform the visualization of the holographic image-guidance. For example, the transformation can be translated, rotated, and/or scaled. The transformed visualization, however, would no longer be precisely aligned with the patient's vasculature.

IV. Methods

Another aspect of the present disclosure can include methods 50, 60 (FIGS. 4 and 5) for providing holographic image-guidance for the non-vascular percutaneous procedures. The methods 50, 60 can be executed by hardware—for example, by the head-mounted device 11 shown in FIG. 1 and described above.

Figure 4:
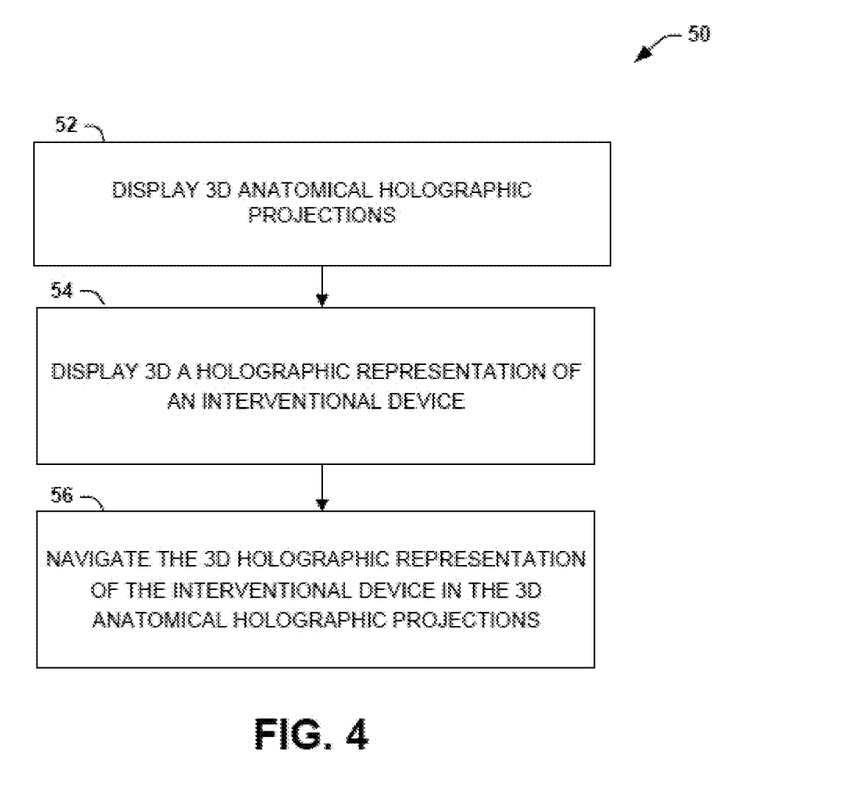
FIGS. 4 and 5 are process flow diagrams of example methods for providing holographic image-guidance for endovascular percutaneous procedures in accordance with another aspect of the present disclosure.
Figure 5:
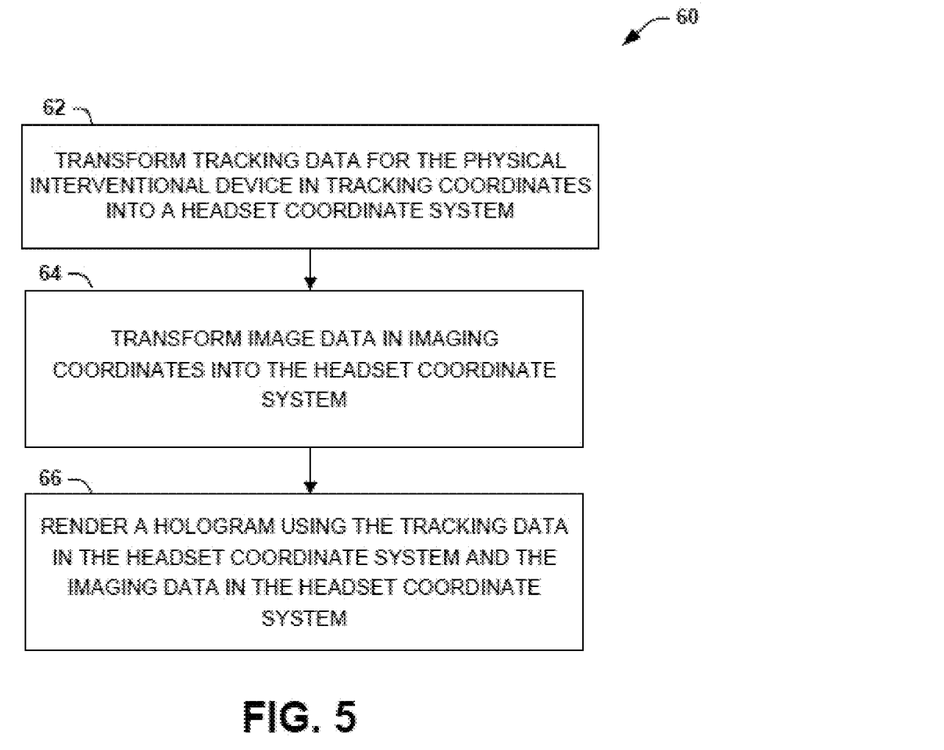

The methods 50 and 60 are illustrated as process flow diagrams with flowchart illustrations. For purposes of simplicity, the methods 50 and 60 shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 50 and 60. Additionally, one or more elements that implement the methods 50 and 60, such as head-mounted device 11 of FIG. 1, may include a non-transitory memory 13 and one or more processors (processing unit 12) that can facilitate the holographic image-guidance.

Referring now to FIG. 4, illustrated is a method 50 for providing and using the holographic image-guidance. The holographic image-guidance can be used to guide an interventional device to a target within the vasculature of a patient's body without requiring intraoperative imaging or in addition to intraoperative imaging. The steps of the method 50 can be performed by the head-mounted device 11 of FIG. 1.

At step 52, 3D anatomical holographic projections of a patient's anatomy (including a portion of the vasculature) can be displayed. The holographic projections can include reference graphics related to a physical operative site with a patient's anatomy. At step 54, a holographic representation of a physical interventional device can be displayed. The holographic representation can include guidance control graphics related to the physical interventional device. At step 56, the 3D holographic representation of the interventional device can be navigated through the 3D anatomical holographic projection. The reference graphics and the guidance control graphics can provide guidance (e.g., visual guidance (pictorial, type, annotation, etc.) and/or auditory guidance) for tracking the physical interventional device through the patient's anatomy using the holographic guidance (using the 3D anatomical holographic projections and the 3D holographic representation of the interventional device). For example, when a line (or graphic) associated with the reference graphics and a line (or graphic) associated with the guidance control graphics intersect, the physical interventional device can be in alignment with a trajectory that would facilitate placement of the physical interventional device within the vasculature. This can be accompanied by a holographic annotation that reports the distance and/or angle deviation from a targeted position or orientation.

The reference graphics and the guidance control graphics can be used to provide event driven guidance. For example, when a stent is within the patient's vasculature, the reference graphics and the guidance control graphics can provide auditory and/or visual guidance as the stent moves. As the stent is moved through the patient's vascular tree, a beep can be used to indicate proximity to a target location for the stent. Similarly, graphics can provide real-time annotations of the position and the orientation of the stent and/or showing the intersection with the target position. In other words, the event driven guidance can inform a user when they are on the right track using one or more event driven signals.

The 3D anatomical holographic projections and the 3D holographic representation of the interventional device are expressed in a common coordinate system. The 3D anatomical holographic projections are created based on image data that is originally in an imaging coordinate system. Similarly, the 3D holographic representation of the interventional device is created based on tracking data that is originally in a tracking coordinate system. FIG. 5 shows a method 60 for registering the coordinates from a tracking system and an imaging system to the common coordinate system (the coordinate system used by a head-mounted device to generate the holograms). Also included are three non-collinear sensor-coils 42 that are used for registration.

A physical interventional device can be integrated with one or more sensor-coils. For a rigid device, one or more sensor-coils can be located at a tip of the physical interventional device. However, for a non-rigid device the sensor-coils are distributed to different points along the physical interventional device. As the physical interventional device traverses a patient's vasculature, the tracking system (e.g., an electromagnetic tracking system) can detect the one or more sensor-coils and provide tracking data (e.g., with six degrees of freedom) in response to the detection. For example, the tracking data can include real-time 3D position data and real-time 3D orientation data. The tracking data can be recorded in a coordinate system of the tracking device and sent to the head-mounted device. At step 62, tracking data for a physical interventional device in tracking coordinates can be transformed into a headset coordinate system (by the head-mounted device).

A patient can undergo a preoperative imaging study that images at least a portion of the underlying anatomy. The preoperative imaging studies can record 3D images (e.g., tomographic images) of the portion of the patient's anatomy. The 3D images can be represented by imaging data (which can be DICOM data), which can be formatted according to an imaging coordinate system of the certain imaging modality that was used to record the imaging data and sent to the head-mounted device. At step 64, image data in imaging coordinates can be transformed to the headset coordinate system (by the head-mounted device). 3D anatomical hierarchical projections generated based on the image data can be based on one or more surface mesh models, multi-planar reformatted images, or the like.

At step 66, a visualization can be rendered (by the head-mounted device) using the tracking data in the headset coordinates and the imaging data in the headset coordinates. The hologram can include a 3D anatomical holographic projection based on the imaging data transformed to the headset coordinates and a 3D holographic representation of the interventional device based on the tracking coordinates. As previously noted, graphics, including the reference graphics and the guidance control graphics, can provide guidance for tracking the physical interventional device through the patient's anatomy using the holographic guidance (using the 3D anatomical holographic projections and the 3D holographic representation of the interventional device). The visualization can be transformed by translating, rotating, and/or scaling to enhance the navigation. The transforming can be triggered by a physical movement of the head-mounted device (e.g., by tilting the head in a particular manner).

V. Example Registration Technique

The following description describes an example registration technique that can be used to register tracking data (in a tracking coordinate system) and imaging data (in an imaging coordinate system) into a common holographic coordinate system utilized by the head-mounted device that provides the holograms. It will be noted that this is a description of just a single example and other registration techniques can be used within the scope of this disclosure.

The registration technique transforms the tracking data and the imaging data into the headset coordinate system. To do so, the head-mounted device can perform two affine transformations: EM-to-HL (or tracking system to head-mounted device) and U-to-HL (or imaging system to head-mounted device). In this example, the transformations rely on co-location of image targets (e.g., fiducial markers placed on the patient's skin and/or anatomical targets) in the different coordinate systems. Three or more image targets can be used that are non-collinear. For example, at least some the image targets must be visible to the tracking system (requiring a sensor-coil on each of the image targets) and a camera associated with the head-mounted device. In some instances, the same or others of the image targets must be visible to the pre-operative imaging system and the camera associated with the head mounted device.

For the EM to HL transformation, two 3D point sets $P_{EM}$ and $P_{H,\ image\ target}$ consisting of corresponding (co-located) point pairs are used: (1) $P_i(x_{hl}, y_{hl}, z_{hl})$ in HL coordinates located with image targets via the head-mounted device and (2) $P_i(x_{EM}, y_{EM}, z_{EM})$ localized with EM sensors (physically associated with the image targets) in EM coordinates for 4 corresponding points. The 3D point sets ($P_{EM}$, $P_{H,\ image\ target}$) are used to determine the EM to HL transformation ($[^{EM}M_{HL}]=LSM\{P_{EM}, P_{H,\ image\ target}\}$) on a processing unit associated with the head-mounted device using a least-square method (LSM). Position and orientation data from the image targets (referred to as landmark sensors) and sensor-coils on the interventional device ($P_{EM,lm,i}(t)$ $[^{EM}M_{HL,cal}]=P_{HL,lm,i}(t)$) are then transformed into HL coordinates using $[^{EM}M_{HL}]$.

With the locations of the landmark sensors and the sensor-coils on the interventional device tracked in HL coordinates the corresponding 3D point sets in the imaging (U) coordinates for the markers and device sensors can also be transformed to HL coordinates. For this, the LSM will also be used to determine a transformation $[^{U}M_{HL}(t)]$, between imaging coordinates and HL coordinates ($[^{U}M_{HL}]=LSM\{P_{U,lm\&d,i}, P_{HL,lm,i}\}$). $[^{U}M_{HL}(t)]$ is then used to transform the imaging coordinates to HL coordinates. This allows the head-mounted device to project the holograms on the patient's vasculature (e.g., in the surgical field).

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The following is claimed:

1. A method comprising:
   receiving, by a head-mounted device comprising a processor, tracking data for a physical interventional device in a tracking coordinate system, wherein the physical interventional device is used during an endovascular percutaneous medical procedure;
   transforming, by the head-mounted device, the tracking data for the physical interventional device in the tracking coordinate system into a headset coordinate system;
   accessing, by the head-mounted device, image data from a pre-operative image of a patient's anatomy comprising a physical operative site in an imaging coordinate system;
   transforming, by the head mounted device, the image data in the imaging coordinate system into the headset coordinate system;
   registering, by the head-mounted device, a 3D holographic representation of the interventional device based on the tracking data for the physical interventional device in the headset coordinate system to 3D anatomical holographic projections of the patient's anatomy based on the imaging data in the headset coordinate system;
   displaying, by the head mounted device, the 3D anatomical holographic projections providing a visualization of a holographic version of the patient's anatomy including a physical operative site within the patient's anatomy; and
   navigating, by the head mounted device, the 3D holographic representation of the interventional device in the 3D anatomical holographic projections based on the tracking data for the interventional device in the headset coordinate system.

2. The method of claim 1, wherein the physical interventional device comprises an integrated sensor-coil that is detectable by a tracking system to provide the tracking data in the tracking coordinate system.

3. The method of claim 2, wherein the tracking data has six-degrees of freedom (6 DOF).

4. The method of claim 2, wherein the tracking data comprises real-time 3D position data and real-time 3D orientation data.

5. The method of claim 2, wherein the sensor coil is located at a tip of the physical interventional device.

6. The method of claim 1, wherein the image data from the pre-operative image of a patient's anatomy is represented by patient-specific DICOM image data from one or more 3D pre-operative tomographic image data sets.

7. The method of claim 1, wherein the 3D anatomical holographic projections are based on one or more surface mesh models or multi-planar reformatted images created from the image data.

8. The method of claim 1, further comprising transforming, by the head mounted device, a visualization of the 3D anatomical holographic projections by at least one of translating, rotating, and scaling to enhance the navigating.

9. The method of claim 8, wherein the transforming is triggered by a physical movement of the head mounted device.

10. The method of claim 1, wherein the transforming further comprises:
locating positions of three or more fiducial markers on the physical patient's anatomy, wherein the positions are in the tracking coordinate system; and
matching the positions of the three or more fiducial markers to three or more locations in the image data in the image coordinate system.

11. The method of claim 10, wherein the positions of the three or more fiducial markers are non-collinear.

12. The method of claim 10, wherein the three or more fiducial markers are sensor-coils placed on the patient's skin.

13. The method of claim 1, wherein the endovascular percutaneous medical procedure comprises an aneurism repair procedure, a stent grafting/placement procedure, a catheterization procedure, a filter placement procedure, an angioplasty procedure, a minimally-invasive catheter procedure, an ablation procedure, a cryoablation procedure, or a guidewire placement procedure.

14. The method of claim 1, wherein the guidance comprises visual feedback or auditory feedback related to location and orientation of the physical interventional device.

15. The method of claim 14, further comprising providing the visual feedback to monitor when a graphic corresponding to the guidance control graphics intersects a graphic corresponding to the reference graphics indicating that the physical interventional device is in alignment with a trajectory that would place the physical interventional device at a target within the patient's vasculature.

16. The method of claim 15, wherein the visual feedback includes a holographic annotation that reports the distance or angle deviation from a targeted position or orientation.

17. A head-mounted device comprising:
a non-transitory memory storing instructions; and
a processor to access the non-transitory memory and execute the instructions to:
receive tracking data for a physical interventional device in a tracking coordinate system, wherein the physical interventional device is used during an endovascular percutaneous medical procedure;
transform the tracking data for the physical interventional device in the tracking coordinate system into a headset coordinate system;
access image data from a pre-operative image of a patient's anatomy comprising a physical operative site in an imaging coordinate system;
transform the image data in the imaging coordinate system into the headset coordinate system;
register a 3D holographic representation of the interventional device based on the tracking data for the physical interventional device in the headset coordinate system to 3D anatomical holographic projections of the patient's anatomy based on the imaging data in the headset coordinate system;
displaying, by the head mounted device, the 3D holographic representation of the interventional device providing a visualization of a holographic version of the interventional device; and
navigating the 3D holographic representation of the interventional device in the 3D anatomical holographic projections based on the tracking data for the interventional device in the headset coordinate system.

18. The head-mounted device of claim 17, further comprising a head mounted display to display the visualization.

19. The head-mounted device of claim 18, wherein the processor further executes the instructions to transform the visualization by at least one of translating, rotating, and scaling to enhance the navigating triggered by a physical movement of the head mounted device.

20. The head-mounted device of claim 17, wherein the transforming further comprises:
locating positions of three or more fiducial markers on the physical patient's skin, wherein the positions are in the tracking coordinate system, wherein the positions are non-collinear; and
matching the positions of the three or more fiducial markers to three or more locations in the image data in the image coordinate system.

* * * * *